(12) United States Patent
Couchourel et al.

(10) Patent No.: US 9,155,757 B2
(45) Date of Patent: Oct. 13, 2015

(54) METHODS AND KITS FOR TREATING VAGINAL AND VULVAR VESTIBULE MUCOSA DISORDERS

(71) Applicant: LABORATOIRES VIVACY, Archamps (FR)

(72) Inventors: Denis Couchourel, Nantes (FR); Elena Fasola, Milan (IT)

(73) Assignee: LABORATOIRES VIVACY, Archamps (FR)

( * ) Notice: Subject to any disclaimer, the term of this patent is extended or adjusted under 35 U.S.C. 154(b) by 0 days.

(21) Appl. No.: 14/047,479

(22) Filed: Oct. 7, 2013

(65) Prior Publication Data

US 2015/0099717 A1   Apr. 9, 2015

(51) Int. Cl.
*A61K 31/70* (2006.01)
*A61K 31/728* (2006.01)
*A61K 31/167* (2006.01)

(52) U.S. Cl.
CPC ............. *A61K 31/728* (2013.01); *A61K 31/167* (2013.01)

(58) Field of Classification Search
CPC .......................... A61K 31/728; A61K 31/167
See application file for complete search history.

(56) References Cited

U.S. PATENT DOCUMENTS

| 7,385,052 | B2 | 6/2008 | Zhao |
| 7,741,476 | B2 | 6/2010 | Lebreton |
| 7,807,656 | B2 * | 10/2010 | Reinmüller ............... 514/54 |
| 2005/0095219 | A1 * | 5/2005 | Yang et al. ............... 424/78.26 |
| 2010/0303873 | A1 | 12/2010 | Piron et al. |
| 2012/0196830 | A1 * | 8/2012 | Parsons ..................... 514/56 |
| 2013/0172288 | A1 | 7/2013 | Bon Betemps et al. |

FOREIGN PATENT DOCUMENTS

| WO | WO 00/46253 A1 | 8/2000 |
| WO | WO 2004/092222 A2 | 10/2004 |
| WO | WO 2009/071697 A1 | 6/2009 |

OTHER PUBLICATIONS

Reed et al., "Pain at the Vulvar Vestibule: A Web-Based Survey," Journal of Lower Genital Tract Disease, vol. 8, No. 1, Jan. 2004, pp. 48-57.

* cited by examiner

*Primary Examiner* — Elli Peselev
(74) *Attorney, Agent, or Firm* — Oliff PLC

(57) ABSTRACT

A method of treating a vaginal or vulvar vestibule mucosa disorder involves administering a composition comprising a hyaluronic acid or a salt thereof to the vagina, vulvar or vulvar vestibule of an individual that has the disorder to treat the disorder. The method may be used to treat vaginal atrophy or vulvar vestibulitis syndrome, among other vulvovaginal mucosa disorders.

23 Claims, No Drawings

METHODS AND KITS FOR TREATING VAGINAL AND VULVAR VESTIBULE MUCOSA DISORDERS

BACKGROUND

The vulvar vestibule (or vulval vestibule) is located between the labia minora. The orifice of the urinary tract (i.e., the urethral orifice) opens into it. The vaginal orifice is behind the vestibule. Its edge is marked by Hart's Line. Hart's Line is the line of change from vulvar skin to the smoother mucosa of the vulva.

Pain at the vulvar vestibule, and at the labia minora, is relatively common. A study by the University of Michigan Journal of Lower Genital Tract Disease: January 2004—Volume 8—Issue 1—pp 48-57 found that about 28% of women have experienced vulvar vestibular pain, and about 8% had the pain in the last 6 months. Some problems could also be due to the vaginal and vulvar dryness.

The human vagina is an elastic muscular canal that extends from the cervix to the vulva. The internal lining of the vagina consists of stratified squamous epithelium and beneath this lining is a layer of smooth muscle, which may contract during sexual intercourse and when giving birth.

The vagina is the connection between the superficial vulva to the cervix of the deep uterus. After menopause, the body produces less estrogen, which causes the vaginal walls to thin out significantly. Some women have severe pain during sexual intercourse or tampon use; severe pain while biking, exercising, or wearing tightly fitting clothing; redness and burning/stinging in the vestibular area and vaginal area; and a frequent urge to urinate.

This pain could be due to vulvar and vaginal atrophy and/or vulvar vestibulitis syndrome (VVS), which is a vaginal condition in which the skin and mucous secreting glands (known as lesser vestibular glands) in the skin become inflamed. This can affect the entire vaginal opening, but predominantly presents in the lower portion. Women of all ages and all levels of sexual activity can experience this uncomfortable condition. The exact cause of vulvar vestibulitis syndrome remains unknown, but researchers continue to work toward gaining more insight into the condition.

Certain factors have been identified as being associated with vulvar vestibulitis syndrome. They include chronic yeast infections, human papilloma virus, chronic bacterial infections, pH imbalance in the vagina (acid-based) and long-term use of irritants and chemicals (like spermicides, lubricants, soaps and detergents).

Others chronic inflammatory pathologies that led to dysuria (pain on urination) and dyspareunia (pain during intercourse) could also be cited, like sclero atrophic lichen that is a chronic inflammatory nature of the anogenital area affecting predominatly women and that is present with genital and extragenital manifestations and as a consequence vulvar region becomes atrophic.

Treatment of all these pathologies often involves steroidal ointments that are topically applied and decrease redness and discomfort. Other options include trichloracetic acid, which works by destroying irritated skin and encouraging the growth of healthy skin; injections of interferon, which helps to increase the body's natural reaction to infection; and, in some cases, surgery (either standard or laser) to remove specific areas of affected skin. In some cases a local or sytemic hormonal treatment could also be associated.

SUMMARY

The present inventors have surprisingly observed that administration by injection of a hyaluronic acid composition could be used to treat vaginal, vulvar and/or vulvar vestibule mucosa disorders.

In embodiments, a method of treating a vaginal, vulvar minora lips or vulvar vestibule mucosa disorder comprises administering by injection a composition comprising a hyaluronic acid or a salt thereof to the vagina, vulvar minora lips or vulvar vestibule of an individual that has the disorder to treat the disorder.

DETAILED DESCRIPTION OF EMBODIMENTS

A method of treating a vaginal or vulvar lips or vulvar vestibule mucosa disorder comprises injecting a composition comprising a hyaluronic acid or a salt thereof into the vagina or vulvar vestibule of an individual that has the disorder to treat the disorder. The individual may be a human or non-human animal. The individual may be female. However, the individual may be a non-biological female having a vagina and/or vulvar vestibule. The method may be used to treat vaginal atrophy or vulvar vestibulitis syndrome, among other vulvovaginal mucosa disorders.

The method may be used to treat chronic inflammatory pathologies, that led to dysuria (pain on urination) and dyspareunia (pain during intercourse), among other sclero atrophic lichen.

Hyaluronic acid is a polysaccharide constituted of repeated disaccharide units of glucuronic acid and N-acetyl glucosamine. Unless context dictates otherwise, "hyaluronic acid" refers to hyaluronic acid and/or a salt thereof. The hyaluronic acid may be crosslinked or not crosslinked, or substituted or not substituted. Hyaluronic acids may be used alone or in combination, such as in a mixture of hyaluronic acids. A mixture of hyaluronic acids may include a plurality of hyaluronic acids, salts thereof, or any combination thereof.

In embodiments, the hyaluronic acid composition is administered by injection. The composition may be administered by one or more injections. The injections may be made into the tissue of the vagina or vulvar vestibule. For example, the composition may be injected by one or more intramucosal injections. Concerning the vaginal mucosa, the injection may be performed in the posterior lower part of the vagina. Injection of the hyaluronic acid composition may be performed using one or more conventional syringes that contain the hyaluronic acid composition or by a multipuncture technique. The multipuncture technique involves a series of injections of small quantities in an area, such that the injections are sufficiently close together to avoid irregularity or empty space Regarding the intravaginal injections, the injections should be performed in the lateral and posterior walls, between 10 and 15 injection sites, using the multipuncture technique in an area 2 ou 3 cm from the vagina entry in the lamina propria. The injections must be superficial, about 1 to 2 mm deep into the mucosa using 30G1/2 needle in a total amount of 0.5 to 0.8 ml of hyaluronic acid composition.

Regarding the vestibule injections, the vestibule area is injected using the multipuncture technique. In embodiments, a total amount of 0.3 ml of the hyaluronic composition is injected using 30G1/2 needle.

In embodiments, the hyaluronic acid composition is administered in an effective amount to treat the vulvovaginal mucosal disorder. The composition may be administered in a single treatment or a series of treatments Function of the dryness and severity of the disorder, the injections should be repeated one, three or six months after the first one injection and each year in maintenance regimen.

In embodiments, the composition is in the form of a gel. For example, the gel may be an injectable hydrogel.

In embodiments, the composition comprises a crosslinked hyaluronic acid and/or salt thereof, alone or in a mixture.

In embodiments, the composition comprises a substituted or unsubstituted hyaluronic acid and/or salt thereof, alone or in a mixture.

In embodiments, the hyaluronic acid is in the form of a potassium or sodium salt.

As an example, sodium hyaluronate exhibits particularly advantageous properties due to its high operating recoil in intradermal injection, and also has excellent rheological properties.

The polysaccharide chains can be characterized by their molecular weight (MW), which is the average molecular weight of the polysaccharide chains and is measured in Daltons (Da).

In embodiments, the polysaccharide chains have a MW from 0.01 MDa to approximately 5 MDa.

In embodiments, the MW is from 0.1 MDa to 3.5 MDa.

In embodiments, the hyaluronic acid is from 0.2 to 5% by weight of the composition. In embodiments, the concentration of hyaluronic acid in the composition is from 2 mg/g to 50 mg/g.

In embodiments, the concentration is from 5 mg/g to 30 mg/g.

The hyaluronic acid may be crosslinked. The degree of crosslinking x is defined by:

x=number of moles of crosslinking agent introduced into the reaction medium/total number of disaccharide units introduced into the reaction medium.

The degree of crosslinking can be controlled by changing several factors, including the molecular weight of the hyaluronic acid, its concentration in the reaction mixture, and the polymer/crosslinking agent ratio.

In embodiments, the degree of crosslinking is from 0.001 to 0.5.

In embodiments, the degree of crosslinking is from 0.01 to 0.25.

In embodiments, the degree of crosslinking is from 0.1 to 0.2.

Numerous substances can be used to crosslink hyaluronic acid, including but not limited to formaldehyde, epoxides, polyaziridyl compounds, divinyl sulfone and others.

In embodiments, the crosslinking agent is 1,4-butanediol diglycidyl ether (BDDE).

In embodiments, the hyaluronic acid is the co-crosslinked hyaluronic acid as described in WO2000/046253 and counterpart U.S. Pat. No. 7,385,052, which are incorporated by reference herein in their entireties.

In embodiments, the hyaluronic acid is a monophasic mixture of hyaluronic acid as described in WO2009/071697 and counterpart U.S. Patent Application Publication No. 2010/0303873, which are incorporated by reference herein in their entireties.

In embodiments, the hyaluronic acid composition is a monophasic mixture of hyaluronic acid as described in WO2004/092222 and counterpart U.S. Pat. No. 7,741,476, which are incorporated by reference herein in their entireties.

In embodiments, the hyaluronic acid composition comprises a substituted hyaluronic acid. Exemplary substituted hyaluronic acids are described in copending U.S. patent application Ser. No. 13/692,511, entitled "Process for the simultaneous substitution and crosslinking of a polysaccharide via its hydroxyl functional groups," filed on Dec. 3, 2012, which is incorporated by reference herein in its entirety.

At present several commercial hyaluronic acid compositions are available, among them the products marketed by the Anteis company under the tradenames ESTHELIS® or FORTELIS®, the products marketed by the Allergan company under the tradenames SURGIDERM®, JUVEDERM® or VOLUMA®, the products marketed by the Q-MED company under the tradename RESTYLANE®, the products marketed by the Teoxane company under the tradename TEOSYAL® or the products marketed by the Vivacy company under the tradename STYLAGE®.

Compositions of the present invention may also contain a safe and effective amount of a local or topical anesthetic.

Examples of anesthetics include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

In embodiments, the amount of anesthetic is from 0.01 to 5% by weight of the total composition.

Compositions may contain a safe and effective amount of one or more antioxidants.

Examples of antioxidants include but are not limited to ascorbic acid and its salts and derivatives, and polyols such as sorbitol, mannitol, and glycerol.

In embodiments, the antioxidant is mannitol.

In embodiments, the amount of antioxidant is from 0.01 to 10% by weight of the total composition.

Compositions of the invention may contain one (or more) active principle(s) dispersed beforehand within them. The term "active principle" is understood to mean any product which is pharmacologically active, including, for example, antiseptic active principles, anti-inflammatory active principles, and the like.

Compositions may generally be prepared by conventional methods such as those known in the art or methods such as those discussed in Application Ser. Nos. 12/746,639 and 13/692,511 which disclosures are incorporated by reference.

Such methods may involve steps of hydration and crosslinking of hyaluronic acid with or without heating, followed by steps of purification and swelling.

In practice, compositions obtained according to processes known in the art, such as after purification and hydration to give the hydrogel, can be packaged, for example in syringes, and sterilized according to known methods (for example, by autoclaving) in order to be sold and/or used directly.

According to another aspect, a kit comprises a composition comprising hyaluronic acid or a salt thereof packaged in a sterile syringe. The kit may include written instructions for performing a method of treating a vaginal or vulvar vestibule mucosa disorder that comprises administering the composition to the vagina or vulvar vestibule of an individual that has the disorder.

EXAMPLES

Crosslinked hyaluronic acid was used to treat vulvovaginal atrophy. 7 patients were enrolled in the study. The median age of enrolled patients was 54.1 years, and their median BMI was 24.5. They had signs and symptoms of vulvovaginal atrophy and had not had any hormone replacement therapy. All symptoms, such as vaginal dryness, dyspareunia, itching, and chafing/irritation, were evaluated by a self-assessed score (0 to 10).

Atrophy was evaluated by a clinical score (0=absent to 4=severe). Vaginal pH and Maturation Index were measured and compared.

0.5-0.8 ml of crosslinked hyaluronic acid (19 mg/ml) that contains mannitol (in order to delay hyaluronic acid degradation) was used per patient.

10-12 injection sites were performed by intramucosal injection into the inferior posterior vagina of each patient. Prior topical anesthesia with 2.5% lidocaine cream was performed on each patient. Scheduled follow-up was at 1 (T1), 3 (T2), 6 (T3), and 12 (T4) months.

The results are the following on vaginal symptoms: dryness and dyspareunia significantly improved for 7 patients in a rapid and sustained manner;

- itching was present in 5 of 7 patients when enrolled (T0), but none of the patients indicating that itching was present at the 3-month follow-up (T2);
- chafing/irritation, present in 7 patients at T0, was indicated as being present by only 3 patients at the 3-month follow-up (T2).

Clinical impression of a steadily improved mucosal trophism and overall doctor satisfaction was high (7.2/10 score at 3 months).

Overall patient satisfaction was also high (7.4/10 score at 3 months).

Moreover, no significant change in mucosal cytology and biology were induced by hyaluronic acid injections as determined at the 3-month follow-up (T2).

The invention claimed is:

1. A method of treating a vaginal or vulvar vestibule mucosa disorder, comprising injecting a composition comprising a hyaluronic acid or a salt thereof into tissue of a vagina or vulvar vestibule of an individual that has the disorder in an amount effective to treat the disorder, wherein the composition is injected by one or more intramucosal injections.

2. The method of claim 1, wherein the disorder is vaginal atrophy.

3. The method of claim 1, wherein the disorder is vulvar vestibulitis syndrome.

4. The method of claim 1, wherein the composition is injected by a multipuncture technique.

5. The method of claim 1, wherein the injection is performed in the posterior lower part of the vagina.

6. The method of claim 1, wherein the hyaluronic acid or salt thereof is from 0.2 to 5% by weight of the composition.

7. The method of claim 1, wherein the hyaluronic acid or salt thereof is at a concentration from 2 to 50 mg/g in the composition.

8. The method of claim 1, wherein the hyaluronic acid or salt thereof is a mixture of hyaluronic acids, salts thereof, or any combination thereof.

9. The method of claim 1, wherein the hyaluronic acid or salt thereof is crosslinked.

10. The method of claim 1, wherein the hyaluronic acid or salt thereof is a mixture of crosslinked and not crosslinked hyaluronic acids.

11. The method of claim 1, wherein the hyaluronic acid or salt thereof is crosslinked with 1,4-butanediol diglycidyl ether (BDDE).

12. The method of claim 1, wherein the hyaluronic acid or a salt thereof is crosslinked and has a degree of crosslinking from 0.001 to 0.5.

13. The method of claim 1, wherein the composition further comprises an antioxidant.

14. The method of claim 13, wherein the antioxidant is from 0.01 to 10% by weight of the composition.

15. The method of claim 1, wherein the composition further comprises mannitol.

16. The method of claim 1, wherein the composition further comprises a local anesthetic.

17. The method of claim 16, wherein the local anesthetic is from 0.01 to 5% by weight of the composition.

18. The method of claim 1, wherein the composition further comprises lidocaine.

19. The method of claim 1, wherein the hyaluronic acid or salt thereof is a potassium or sodium salt of hyaluronic acid.

20. The method of claim 1, wherein the hyaluronic acid or salt thereof is sodium hyaluronate.

21. The method of claim 1, wherein the hyaluronic acid or salt thereof has polysaccharide chains with an average molecular weight from 0.01 MDa to approximately 5 MDa.

22. The method of claim 1, wherein the hyaluronic acid or salt thereof is substituted.

23. The method of claim 1, wherein the composition is a hydrogel.

* * * * *